United States Patent
Anderson et al.

(10) Patent No.: US 10,512,759 B2
(45) Date of Patent: Dec. 24, 2019

(54) WEEPING BALLOON DEVICES

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: James M. Anderson, Corcoran, MN (US); David Raab, Roseville, MN (US); Adam David Grovender, Maple Grove, MN (US); Roger W. McGowan, Ostego, MN (US)

(73) Assignees: BOSTON SCIENTIFIC SCIMED, INC, Maple Grove, MN (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 15/491,651

(22) Filed: Apr. 19, 2017

(65) Prior Publication Data

US 2017/0296793 A1 Oct. 19, 2017

Related U.S. Application Data

(60) Provisional application No. 62/324,424, filed on Apr. 19, 2016.

(51) Int. Cl.
*A61B 1/00* (2006.01)
*A61B 17/00* (2006.01)
(Continued)

(52) U.S. Cl.
CPC ....... *A61M 25/10* (2013.01); *A61B 17/00234* (2013.01); *A61B 90/361* (2016.02);
(Continued)

(58) Field of Classification Search
CPC .... A61M 2025/1086; A61M 2025/105; A61M 25/104; A61B 90/37
(Continued)

(56) References Cited

U.S. PATENT DOCUMENTS

| 4,784,133 A | 11/1988 | MacKin |
| 4,961,738 A | 10/1990 | MacKin |

(Continued)

FOREIGN PATENT DOCUMENTS

| CA | 2495562 A1 | 2/2004 |
| EP | 1870018 A2 | 12/2007 |

(Continued)

OTHER PUBLICATIONS

Invitation to Pay Additional Fees dated Aug. 10, 2017 from the International Application No. PCT/US2017/028387.

*Primary Examiner* — Theodore J Stigell
(74) *Attorney, Agent, or Firm* — Seager, Tufte & Wickhem, LLP

(57) ABSTRACT

Catheters with weeping balloons can be used for various medical purposes. For example, in some embodiments provided herein weeping balloons are used for catheter visualization devices. In some embodiments, weeping balloons are used to deliver therapeutic agents. Weeping balloons can include openings of a selected size and shape through which a fluid gradually flows or "weeps." The design of the openings can affect performance characteristics such as, but not limited to, fluid flow rate, tear resistance, and mitigation of counter-flow.

14 Claims, 8 Drawing Sheets

(51) Int. Cl.
*A61B 90/00* (2016.01)
*A61M 25/10* (2013.01)

(52) U.S. Cl.
CPC ........... *A61B 90/37* (2016.02); *A61M 25/104* (2013.01); *A61B 1/00082* (2013.01); *A61M 25/1011* (2013.01); *A61M 2025/1004* (2013.01); *A61M 2025/105* (2013.01); *A61M 2025/1075* (2013.01); *A61M 2025/1084* (2013.01); *A61M 2025/1086* (2013.01); *A61M 2025/1088* (2013.01); *A61M 2210/125* (2013.01)

(58) Field of Classification Search
USPC ........................................ 604/103.01, 103.02
See application file for complete search history.

(56) References Cited

U.S. PATENT DOCUMENTS

| | | |
|---|---|---|
| 5,254,089 A | 10/1993 | Wang |
| 5,709,653 A | 1/1998 | Leone |
| 5,762,604 A | 6/1998 | Kieturakis |
| 5,833,682 A | 11/1998 | Amplatz et al. |
| 5,876,426 A | 3/1999 | Kume et al. |
| 5,964,751 A | 10/1999 | Amplatz et al. |
| 6,517,533 B1 | 2/2003 | Swaminathan |
| 6,808,518 B2 * | 10/2004 | Wellman ............ A61M 25/1011 604/103.08 |
| 8,827,953 B2 * | 9/2014 | Rocha-Singh .......... A61F 2/945 604/101.02 |
| 2003/0158517 A1 | 8/2003 | Kokish |
| 2005/0119523 A1 | 6/2005 | Starksen et al. |
| 2005/0197530 A1 | 9/2005 | Wallace et al. |
| 2005/0245882 A1 | 11/2005 | Elkins et al. |
| 2008/0015500 A1 * | 1/2008 | Herweck ............... A61L 29/085 604/103.01 |
| 2009/0143640 A1 | 6/2009 | Saadat et al. |
| 2009/0198216 A1 | 8/2009 | Muni et al. |
| 2010/0249749 A1 * | 9/2010 | Cheng .................. A61L 29/085 604/509 |
| 2012/0041412 A1 * | 2/2012 | Roth ..................... A61M 25/10 604/500 |
| 2014/0249563 A1 | 9/2014 | Mahli |
| 2016/0045098 A1 | 2/2016 | Tsubouchi |

FOREIGN PATENT DOCUMENTS

| | | |
|---|---|---|
| EP | 2508222 A1 | 10/2012 |
| WO | 2004039445 A1 | 5/2004 |
| WO | 2007147060 A2 | 12/2007 |
| WO | 2013159066 A1 | 10/2013 |

* cited by examiner

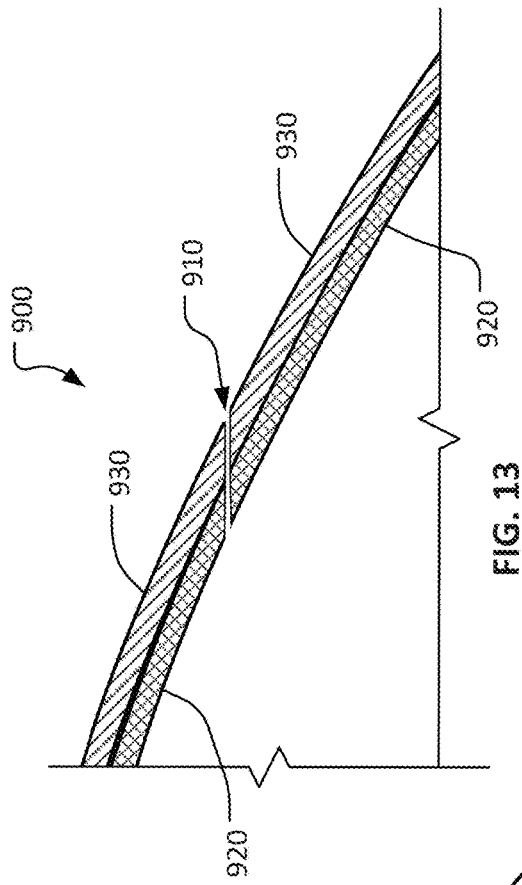
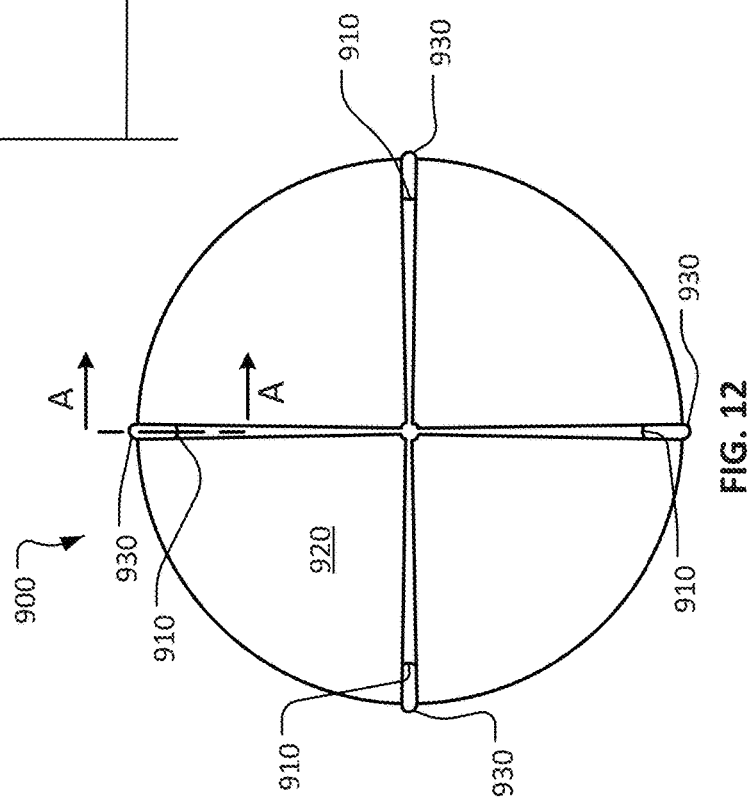

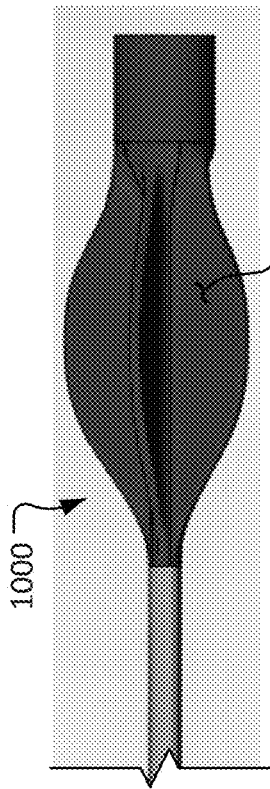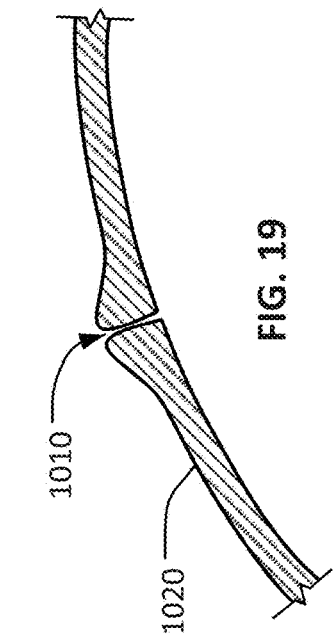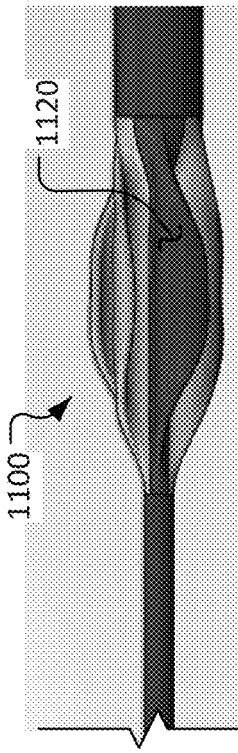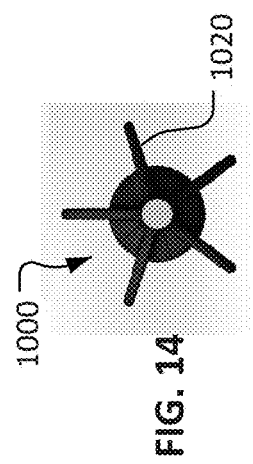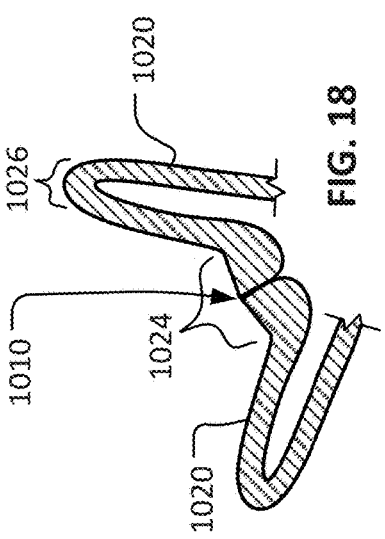

WEEPING BALLOON DEVICES

CROSS-REFERENCE TO RELATED APPLICATIONS

This application claims priority under 35 U.S.C. § 119(e) to U.S. Provisional Application No. 62/324,424, filed Apr. 19, 2016, the entire disclosure of which is herein incorporated by reference.

TECHNICAL FIELD

This disclosure relates to medical devices such as catheter-based weeping balloon devices. In one example implementation this disclosure relates to weeping balloon catheter visualization devices. This disclosure also relates to various hole designs of the weeping balloons.

BACKGROUND

The presence and movement of opaque bodily fluids such as blood generally make in vivo imaging of tissue regions within a patient difficult. Medical devices may therefore, in some cases, be used to visualize interior regions of a patient's body by depicting a visual construct. For example, ultrasound devices may be used to produce in vivo ultrasound images from within a body. In another example, mapping devices having position sensors for generating a map depicting a two- or three-dimensional image of a patient's interior region may also be used. Visual information provided by such devices can often be limited because, for example, the mapping device may not be able to provide visual information of the tissue surface condition within a heart chamber. Thus, there is a need for medical devices that can provide improved visualization for viewing a blood-filled cavity or vessel within the patient.

Medical devices may, in some cases, use an inflatable imaging balloon to obtain in vivo imaging of the patient's tissue regions. The imaging balloon can be introduced into the patient's body in a deflated state. Once introduced, the imaging balloon can be inflated and pressed against a targeted tissue region for imaging. Imaging can be achieved by use of an optical fiber or other electronic apparatus for viewing tissue through the wall of the inflated balloon.

Imaging balloons may encounter issues that affect the quality of the image being captured. For example, because of intervening blood between the balloon and tissue, imaging balloons may produce poor or blurred tissue images if the balloon is not firmly pressed against the tissue surface.

SUMMARY

This disclosure provides medical devices such as catheters with weeping balloons. For example, this disclosure provides weeping balloon catheter visualization devices and hole designs of the weeping balloons. The balloon catheter visualization devices, systems and methods provided herein include features that improve minimally invasive surgical techniques used during procedures such as, but not limited to, heart valve repair procedures. While some of the devices, systems and methods provided herein are described in the context of a tricuspid valve repair, other types of minimally invasive surgical procedures are also envisioned within the scope of this disclosure. For example, the systems and methods provided herein may also be advantageously applied to tissue repair procedures in the other areas of the heart, peripheral vasculature and other locations within the body.

In some aspects, a weeping balloon device includes a catheter shaft defining a lumen and an inflatable balloon attached to the catheter shaft. The balloon includes a balloon wall that defines an interior space in fluid communication with the lumen. The balloon wall also defines a plurality of openings in fluid communication with the interior space. The weeping balloon device also includes, at each opening of the plurality of openings, at least one additional layer of material attached to the balloon wall to reinforce the structure around openings.

Such a weeping balloon device may optionally include one or more of the following features. Each additional layer of material may define an additional opening that is concentric with an opening of the plurality of openings defined by the balloon wall. In some embodiments, at least one of the additional layers of material does not define any openings. In various embodiments, an open region between the at least one additional layer of material and the balloon wall provides a passageway in fluid communication with the opening through the balloon wall that is at the at least one additional layer of material. At least one of the additional layers of material may define a plurality of additional openings that are in fluid communication with the opening through the balloon wall that is at the at least one additional layer of material. In some embodiments, the plurality of additional openings are smaller than the opening through the balloon wall that is at the at least one additional layer of material. In particular embodiments, none of the plurality of additional openings are coincident with the opening through the balloon wall that is at the at least one additional layer of material. At least one opening of the plurality of openings may be a slit. In some embodiments, at least one end of the slit is formed to include a stress concentration relief shape.

In some aspects, a weeping balloon device includes a catheter shaft defining a lumen and an inflatable balloon attached to the catheter shaft. The balloon includes a balloon wall defining an interior space in fluid communication with the lumen. The balloon wall also defines a plurality of openings in fluid communication with the interior space. The weeping balloon device also includes a plurality of ribs projecting from a surface of the balloon wall. A respective rib of the plurality of ribs is located at each opening of the plurality of openings, and a respective opening of the plurality of openings extends through the respective rib.

Such a weeping balloon device may optionally include one or more of the following features. At least one opening of the plurality of openings may be a slit. In some embodiments, the slit does not extend radially in relation to the balloon. The plurality of ribs may project from an exterior surface of the balloon wall. In some embodiments, the plurality of ribs are integrally formed with the balloon wall.

In some aspects, a weeping balloon device includes a catheter shaft defining a lumen and an inflatable balloon attached to the catheter shaft. The balloon includes a balloon wall defining an interior space in fluid communication with the lumen. The balloon wall also defines a plurality of openings in fluid communication with the interior space. The plurality of openings are defined in areas of the balloon wall that, while the balloon is not fully inflated, are depressed radially inward in comparison to other areas of the balloon wall. While the balloon is not fully inflated, the plurality of openings are sealed, and while the balloon is fully inflated, the plurality of openings are open.

Such a weeping balloon device may optionally include one or more of the following features. While the balloon is fully deflated, the balloon wall may define folds and the plurality of openings can be located in crotches between adjacent folds. In some embodiments, in the folds extend radially along generally linear paths. In some embodiments, the folds extend radially along curved paths. While the balloon is partially inflated, the balloon wall may define localized depressions, and the openings may be located in the localized depressions. In some embodiments, while the balloon is fully inflated, the localized depressions are eliminated.

The details of one or more embodiments of balloon catheter visualization devices, systems, and methods provided herein are set forth in the accompanying drawings and the description below. Other features, objects, and advantages will be apparent from the description and drawings, and from the claims.

DESCRIPTION OF DRAWINGS

FIG. 12 is a distal end view of another weeping balloon device in accordance with some embodiments.

FIG. 13 is a cross-sectional view of a portion of the weeping balloon device of FIG. 12.

FIG. 14 is an end view of another weeping balloon device in accordance with some embodiments. The balloon is shown in an uninflated configuration.

FIG. 15 is a side view of the weeping balloon device of FIG. 14.

FIG. 16 is an end view of another weeping balloon device in accordance with some embodiments. The balloon is shown in an uninflated configuration.

FIG. 17 is a side view of the weeping balloon device of FIG. 14.

FIG. 18 is a cross-sectional view of a portion of the weeping balloon devices of FIGS. 14-17. The cross-sectional view is shown with the balloon in an uninflated configuration.

FIG. 19 is a cross-sectional view of a portion of the weeping balloon devices of FIGS. 14-17. The cross-sectional view is shown with the balloon in an inflated configuration.

DETAILED DESCRIPTION

Catheters with weeping balloons can be used for various medical purposes. For example, in some embodiments weeping balloons are used for catheter visualization devices. In some embodiments, weeping balloons are used to deliver therapeutic agents. Weeping balloons can include openings of a selected size and shape through which a fluid gradually flows or "weeps." As described further below, the design of the openings can affect performance characteristics such as, but not limited to, fluid flow rate, tear resistance, and mitigation of counter-flow.

Balloon catheter visualization device, systems, and methods provided herein can allow for balloon catheter visualization of a target location, which can provide anatomy and pathology identification as well as device placement visual feedback to the physician user during a minimally invasive method. Balloon catheter visualization devices, systems, and methods provided herein can include an elongate, compliant balloon having a transparent wall. In some cases, the transparent wall can include portions arranged to be sutured to an anatomical location through the transparent wall and to separate from the remainder of the balloon catheter. In some case, the balloon can include pores to allow for the balloon to "weep" to provide a visually clear area surrounding the balloon. In some cases, the balloon wall (e.g., a transparent balloon wall) can have a structure that limits the propagation of tears. In some cases, the balloon can include polymeric fibers within the balloon material.

Figure 1:
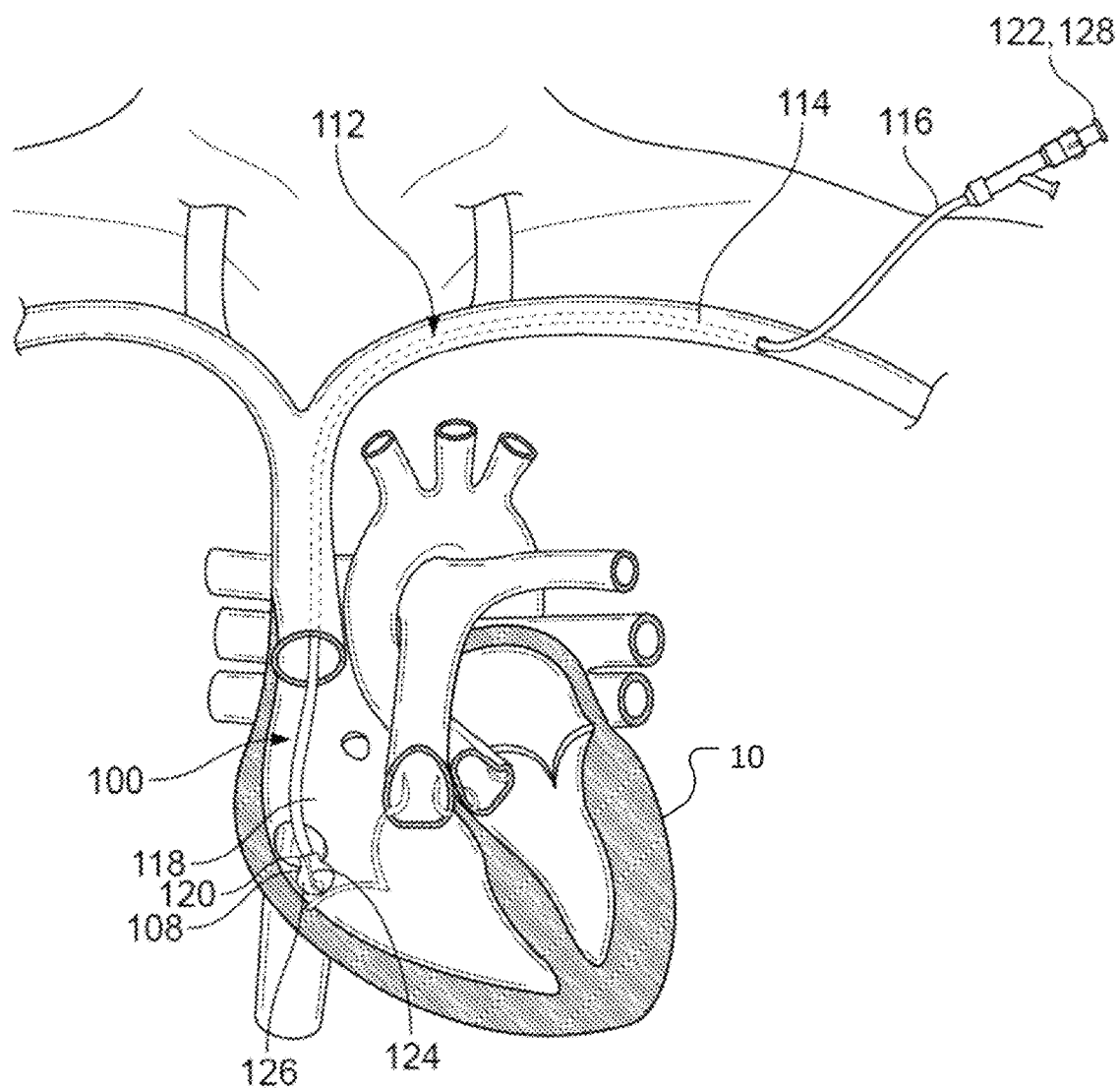
FIG. 1 is an illustration of an exemplary balloon catheter visualization device within a human anatomy.

Referring to FIG. 1, an exemplary balloon catheter visualization system 100 can be used to visualize tissue structures within a human anatomy. In some cases, balloon catheter visualization system 100 can be inserted into a right atrium of a heart 10 through a brachial vein or a jugular vein. Balloon catheter visualization system 100 includes a tubular body 112 (which can also be described as an elongate shaft or catheter) having a proximal end portion 114 with a proximal end 116 and a distal end portion 118 with a distal end 120. In some embodiments, proximal end portion 114 can couple to a catheter hub 122 or a manifold. In the depicted embodiment, the distal end portion 118 includes an integrated camera (not shown), a fastening tool 124 with a fastener and at least one balloon 108 (also described as balloon member).

In some embodiments, the integrated camera and fastening tool 124 can be disposed within balloon 108. As shown in FIG. 1, balloon 108 can form a distal tip of balloon catheter visualization system 100. In some embodiments, balloon 108 is a weeping balloon. That is, balloon 108 can be configured to slowly transmit fluid through a wall of balloon 108, as described herein. Such fluid can be visually clear or transparent and can displace blood that would otherwise obscure visualization of areas adjacent to the balloon 108. In some embodiments, as described further below, the portions of the balloon 108 that are configured to slowly transmit fluid can be advantageously designed to resist expansion while under pressure, resist tearing, and to resist blood reflux, for example. Accordingly, the weeping balloon design embodiments provided herein provide improved performance in comparison to prior conventional weeping balloon devices.

In some embodiments, the fastening tool 124 can pass a fastener through the balloon 108 to suture an anatomical location outside the balloon. The balloon 108 can be filled with an inflation medium, such as saline solution, that can be safely delivered to the patient, thus leakage from resulting openings in the balloon 108 caused by the passing of the fastener through the balloon 108 can be tolerated.

In some embodiments, balloon catheter visualization system 100 includes at least one tubular body 112 defining a lumen (not shown). In some cases, balloon catheter visualization system 100 can include multiple tubular bodies, in which each tubular body defines at least one lumen. Each tubular body 112 can optionally include multiple lumens, for example, coaxial or non-coaxial lumens. Balloon catheter visualization system 100 can have one or more lumens that extend partially or fully thorough one or more tubular bodies 112. One or more lumens can be used as a conduit adapted to receive components, e.g., integrated camera or fastener tools, and/or inflation media, e.g., saline. In some cases, one or more lumens can be adapted to jet inflation media, e.g., saline, into distal end portion 118 of balloon catheter visualization device 100.

In some embodiments, catheter hub 122 generally connects an external fluid supply to one or more lumens of balloon catheter visualization system 100. Catheter hub 122 can include one or more ports 128 to facilitate a fluid connection to another medical device or a fluid source. For example, port 128 can supply saline solution into one or more lumens of tubular body 112. Catheter hub 122 may be coupled to tubular body 112 directly or indirectly. In some cases, a flexible tubing, sometimes referred to as a strain relief tubing, is coupled between manifold 122 and the tubular body 112 at the proximal end 116 to provide a longitudinal tapered transition between catheter hub 122 and tubular body 112. Flexible tubing can help to increase kink resistance of tubular body 112 at proximal end portion 114.

Figure 2:
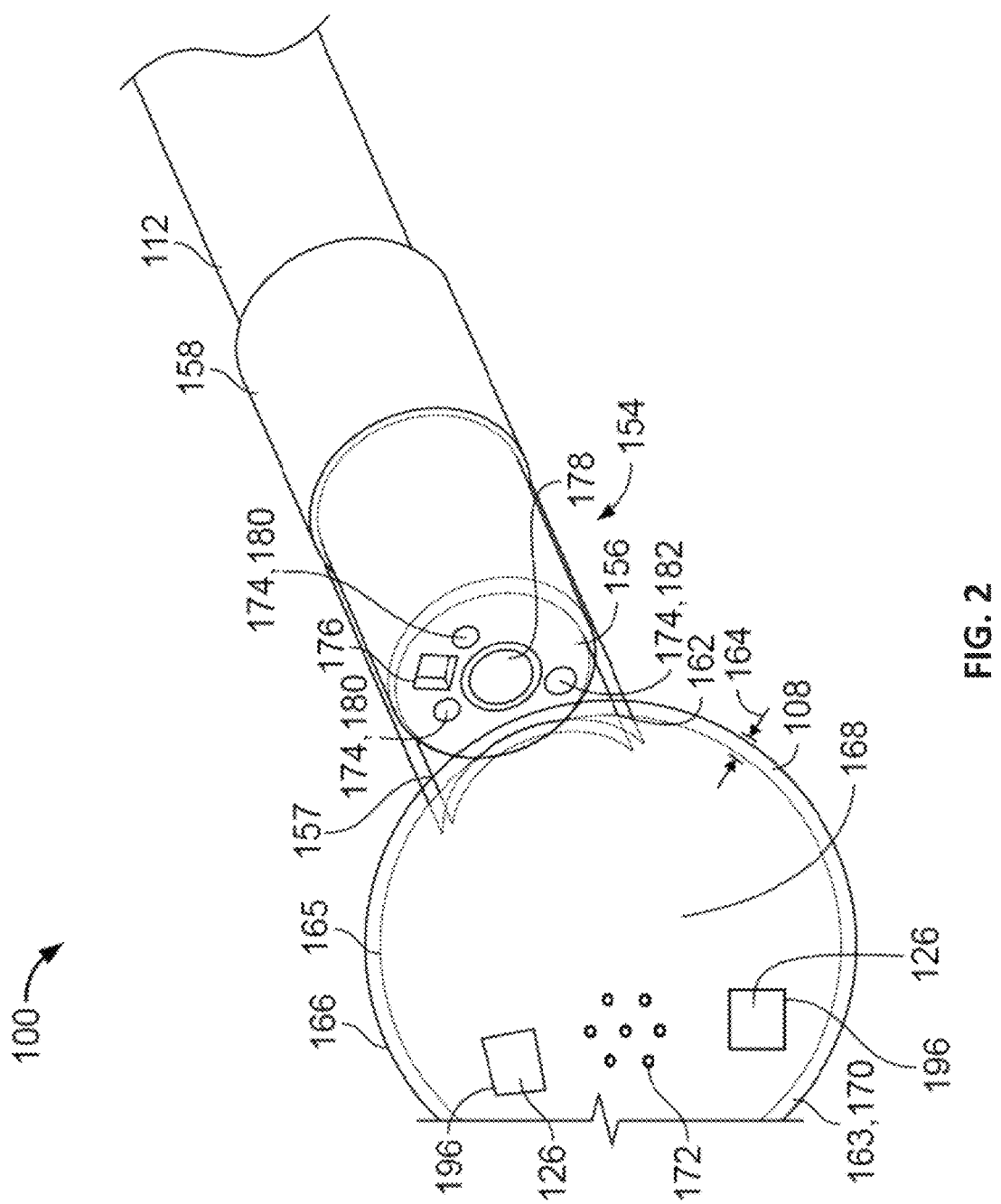
FIG. 2 is a perspective view of a distal end portion of an exemplary balloon catheter visualization device.

Referring to FIG. 2, a distal end of exemplary balloon catheter visualization system 100 can include the balloon 108. In some embodiments, the exterior surface of balloon 108 (which can be primarily silicone, for example) may have a hydrophilic coating to further enhance navigation, lubricity, surface wetting, and visual quality. Such a coating may also reduce traumatic abrasion to anatomy and tissues. Such coatings may be dipped, sprayed, or deposited on the exterior surface of balloon 108. In some embodiments, the exterior surface of balloon 108 may include a matrix lamination such as electrospun hydrophilic materials. In particular embodiments, the inner surface of balloon 108 may have a hydrophilic coating that may also enhance visual quality/clarity.

In some embodiments, the balloon 108 includes tear lines 196, or weakened sections, in the balloon wall 164 that define pledgets 126. In some embodiments, pledgets 126 are adapted to be sutured to anatomical locations and separated from balloon 108. The balloon catheter visualization system 100 can include an elongate, tubular body 112 with a distal end portion 154. A distal end 156 of distal end portion 154 can be either directly or indirectly coupled to a balloon 108. For example, tubular body 112 can be coupled to balloon 108 indirectly by using an intermediate catheter shaft 157. The intermediate catheter shaft 157 can couple to a proximal end 162 of balloon 108 and a catheter interface portion 158 of tubular body 112.

In some embodiments, balloon 108 is disposed at or near to distal end 156 of tubular body 112. Balloon 108 can include the proximal end 162, a distal end 163 and a wall 164 that extends from an interior surface 165 to an exterior surface 166. In the depicted embodiment, balloon 108 forms a distal tip 170 of balloon catheter visualization system 100. As described further herein, balloon 108 can be filled with an inflation media in an interior cavity 168 defined between proximal and distal ends 162, 163. Balloon 108 can be a weeping balloon device, i.e., a balloon structure that defines one or more openings or perforations 172 extending through wall 164. Balloon 108 can have a distal face that defines openings 172 of the weeping balloon 108. In such a case, the distal face of the balloon 108 can be abutted to tissue and the tissue can be visualized using the balloon catheter visualization system 100.

Still referring to FIG. 2, in some embodiments distal end of tubular body 112 can include a plurality of lumens 174. Each lumen of plurality of lumens 174 can longitudinally extend within tubular body 112 (entirely or partially therethrough). Each lumen 174 can be formed from one of various cross-sectional shapes, e.g., circle, oval, slot, square, rectangular, triangular, trapezoid, rhomboid, or irregular shape. The shape of the lumen may facilitate receiving other components of balloon catheter visualization system 100. For example, one or more lumens 174 can be used to receive a fastening tool (not shown), a camera 176, fiber optic light cables (not shown), electrical cables (not shown), inflation media, and combinations thereof. In some embodiments, tubular body 112 defines a central lumen 178 for receiving a fastening tool (not shown) for delivering a fastener (not shown), two or more lumens for receiving fiber optic light cables 180, one or more lumens for delivering inflation media 182, and one or more lumens for receiving camera 176.

In some embodiments, balloon 108 of balloon catheter visualization system 100 is a weeping balloon. A weeping balloon 108, in the context of the present disclosure, includes a balloon structure defining one or more perforations 172 (also described as apertures, hole, slits, openings, pores, micropores, etc., extending through a balloon wall). As such, weeping balloons 108 can transfer fluid through the balloon wall 164, from the interior cavity 168 to the exterior surface 166 of balloon 108. Transferring fluid (e.g., inflation media) to exterior surface 166 can provide a benefit of displacing blood from exterior surface 166 of balloon 108 that would otherwise blur or obstruct visual imaging through balloon 108. In other words, inflation media transferred through the one or more openings 172 can help keep the exterior surface 166 of balloon 108 visually clear. When a plain balloon is placed against an anatomical surface, blood can be trapped on the balloon surface and thus obscure the view, but inflation media (e.g., saline) exiting the openings 172 of a weeping balloon 108 can wash away this blood on the balloon surface adjacent to the anatomical surface.

In some embodiments, a weeping balloon 108 used in a balloon catheter visualization system 100 or other medical device has at least 3 openings 172. In some embodiments, weeping balloons 108 used in balloon catheter visualization systems 100 or other medical devices can have between 3 and 10,000 openings, between 3 and 1,000 openings, between 3 and 100 openings, or between 3 and 10 openings, or between 4 and 10 openings, or between 5 and 10 openings, or between 6 and 10 openings, or between 7 and 10 openings, or between 8 and 10 openings, 9 openings, 10 openings, or between 10 and 12 openings, or between 10 and 15 openings, or between 10 and 20 openings, or more than 20 openings are included in the weeping balloons provided herein.

In some cases, particularly in cases where the number of openings is within the above ranges, the number and dimensions of openings in a weeping balloon 108 used in a balloon catheter visualization system 100 or other medical device allows for a fluid flow rate of between about 1 and about 50 ml/minute. In some cases, the number and dimensions of openings in a weeping balloon 108 described herein provide a fluid flow rate between about 3 ml/minute and about 10 ml/minute. In some cases, a weeping balloon 108 used in balloon catheter visualization systems 100 and other medical devices can have a plurality of openings that perfuse fluid (e.g., an inflation media such as saline) through the balloon and into the blood. In some cases, a weeping balloon 108 used in a balloon catheter visualization system 100 or device provided herein can have a greater opening density in portions of the balloon wall 164 in the center of the field of view and a lower opening density around a periphery of the field of view.

While a visualization system 100 is used to describe the weeping balloons 108 provided herein, it should be understood that the visualization system 100 is just one example implementation. The weeping balloon devices provided herein can be used in various other implementations. For example, in some embodiments the weeping balloon devices provided herein can be used to deliver a therapeutic agent.

Figure 3:
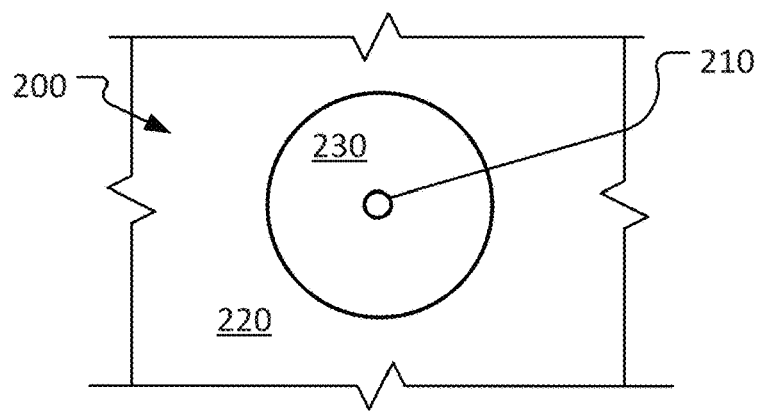
FIG. 3 is a plan view of a portion of a weeping balloon device in accordance with some embodiments.
Figure 4:
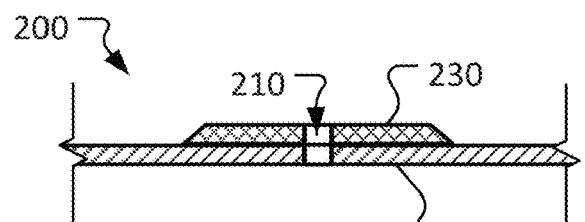
FIG. 4 is a cross-sectional view of the portion of the weeping balloon device of FIG. 3.

Referring to FIGS. 3 and 4, a weeping balloon 200 can define an opening 210 through which fluid can pass. While a single opening 210 is depicted in this portion of weeping balloon 200, it should be understood that, as described above, any number of such openings 210 can be included in the weeping balloon 200.

Weeping balloon 200 is designed with features that are directed to keeping the size of opening 210 substantially consistent even with fluctuations in the fluid pressure internal to the balloon 200. In particular, weeping balloon 200 includes a layer of reinforcement material 230 that is laminated on the balloon wall 220 around the opening 210. Both the balloon wall 220 and the reinforcement material 230 define the opening 210.

The reinforcement material 230 supplements the stiffness of balloon wall 220 around opening 210 to provide greater resistance to the deformation of opening 210 that might otherwise occur without the presence of the reinforcement material 230. For example, as the fluid pressure within the internal space defined by the weeping balloon 200 increases, the balloon wall 220 will tend to stretch. The stretching of the balloon wall 220 will tend to enlarge the opening 210. Such enlarging of the opening 210 may be undesirable in some cases. For example, as the opening 210 enlarges, the opening 210 may become too large and, in result, too much fluid may be transmitted through opening 210.

To resist the enlarging of opening 210, the material stiffness around opening 210 can be increased by adding the reinforcement material 230. At other areas of the balloon 200, the single layer balloon wall 220 (without the reinforcement material 230) can provide a higher compliance to allow for a desired low-profile collapsibility of balloon 200, for example.

In some embodiments, the reinforcement material 230 is a different material than the balloon wall 220. For example, in some embodiments the reinforcement material 230 is made of polyether block amide (e.g., PEBAX®) while the balloon wall 220 is made of silicone (e.g., about 30 A durometer). It should be understood that other combinations of materials are also envisioned. In another non-limiting example, the balloon wall 220 is made of silicone at a first durometer (e.g., about 30 A durometer) and the reinforcement material 230 is made of silicone at a second durometer (e.g., about 50 A durometer).

The reinforcement material 230 is attached to the balloon wall 220. In some cases, an adhesive is used to bond the reinforcement material 230 to the balloon wall 220. For example, in some cases a UV curable silicone adhesive is used to bond the reinforcement material 230 to the balloon wall 220. Other types of adhesives can also be used. In some cases, the reinforcement material 230 is molded onto the balloon wall 220.

While in the depicted embodiment the reinforcement material 230 is a circular shape, in some embodiments the reinforcement material 230 has a different shape. For example, in some embodiments the reinforcement material 230 is ovular, elliptical, rectangular, triangular, polygonal, e.g., and the like. Further, the thickness of the reinforcement material 230 can be constant or variable. For example, the outer edges of the reinforcement material 230 can have a tapered shape away from the opening 210.

As described above, both the reinforcement material 230 and the balloon wall 220 define the opening 210. In the depicted embodiment, the opening 210 is the same size in each of the reinforcement material 230 and the balloon wall 220. In some embodiments, the opening defined by the reinforcement material 230 is larger than the opening defined by the balloon wall 220. In some embodiments, the opening defined by the reinforcement material 230 is smaller than the opening defined by the balloon wall 220. For example, in some embodiments the diameters of the openings defined by the reinforcement material 230 and the balloon wall 220 differ by about 5% to about 15%, or about 10% to about 20%, or about 15% to about 25%, or about 20% to about 30%, or about 25% to about 35%, or about 30% to about 40%, or more than about 40%.

While in the depicted embodiment the opening 210 is circular, in some embodiments the opening 210 has a different shape. For example, in some embodiments the opening 210 is a slot, a slit, ovular, elliptical, rectangular, triangular, and the like. In some embodiments, different shapes may be used for the openings 210 at different locations on the weeping balloon 200.

Figure 5:
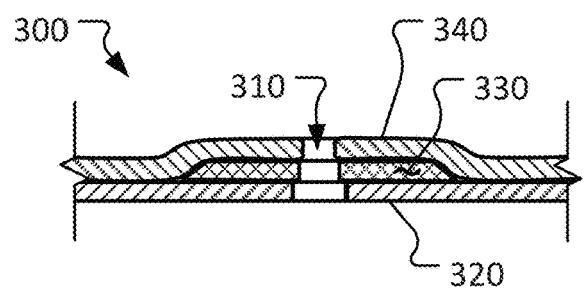
FIG. 5 is a cross-sectional view of a portion of another weeping balloon device in accordance with some embodiments.

Referring to FIG. 5, another example weeping balloon 300 can be configured to resist deformation of an opening 310 through which fluid can pass. While a single opening 310 is depicted in this portion of weeping balloon 300, it should be understood that, as described above, any number of such openings 310 can be included in the weeping balloon 300.

The laminated construction of weeping balloon 300 includes a first balloon wall layer 320, a reinforcement material 330, and a second balloon wall layer 340. The reinforcement material 330 is sandwiched between the first balloon wall layer 320 and the second balloon wall layer 340. In some embodiments, the second balloon wall layer 340 extends all around the balloon 300 (thereby serving as a contiguous outer surface of the entire balloon 300). In some embodiments, the second balloon wall layer 340 is a localized layer that does not extend all around the balloon 300.

Various materials can be used for the first balloon wall layer 320, reinforcement material 330, and second balloon wall layer 340. In one non-limiting example, the first balloon wall layer 320 is silicone, the reinforcement material 330 is PEBAX®, and the second balloon wall layer 340 is silicone. Other materials are also envisioned.

In some embodiments, the first balloon wall layer 320 can be formed by dip-molding, then the reinforcement material 330 can be bonded to the first balloon wall layer 320. After that, a second dip-molding can form the second balloon wall layer 340 on top of the first balloon wall layer 320 and the reinforcement material 330. Alternatively, the second balloon wall layer 340 can be bonded onto the first balloon wall layer 320 and the reinforcement material 330.

The opening 310 can include any of the variations (e.g., shapes, sizes, etc.) described above in reference to the opening 210. For example, in the depicted embodiment the opening 310 defined by the first balloon wall layer 320 is larger than the opening 310 defined by the reinforcement material 330 and the second balloon wall layer 340. In addition, the opening 310 defined by the second balloon wall layer 340 is smaller than the opening 310 defined by the reinforcement material 330 and the first balloon wall layer 320. In some embodiments, the opening 310 defined by the reinforcement material 330 is larger than the openings 310 defined by the first and second balloon wall layers 320 and 340. Any such combinations of differing or equivalent sizes of opening 310 (in the various layers) can be utilized and are within the scope of this disclosure.

Figure 6:
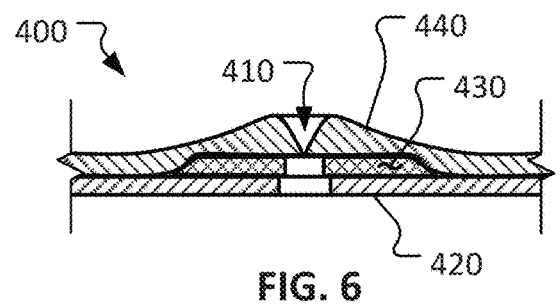
FIG. 6 is a cross-sectional view of a portion of another weeping balloon device in accordance with some embodiments.

Referring to FIG. 6, another example weeping balloon 400 can be configured to resist deformation of an opening 410 through which fluid can pass. While a single opening 410 is depicted in this portion of weeping balloon 400, it should be understood that, as described above, any number of such openings 410 can be included in the weeping balloon 400.

In this example, the multi-layer construction (i.e., first balloon wall layer 420, reinforcement material 430, and second balloon wall layer 440) around opening 410 is similar to that of weeping balloon 300 except that the second balloon wall layer 440 is configured differently. In particular, in the depicted embodiment the second balloon wall layer 440 includes a thicker area surrounding the opening 410 and the opening 410 defined by the second balloon wall layer 440 is conical or tapered (e.g., a tapered slit). Such a design may help seal opening 410 to thereby resist inflow of blood into the interior of the weeping balloon 400.

Example weeping balloon 400 illustrates that the thickness of the layers 420, 430, and/or 440 need not be uniform. For example, in the depicted embodiment the second balloon wall layer 440 includes a thicker area surrounding the opening 410. Such a variation in thickness can be incorporated into any of the layers 420, 430, and/or 440 of the weeping balloon 400 and into any of the other weeping balloon embodiments provided herein.

Figure 7:
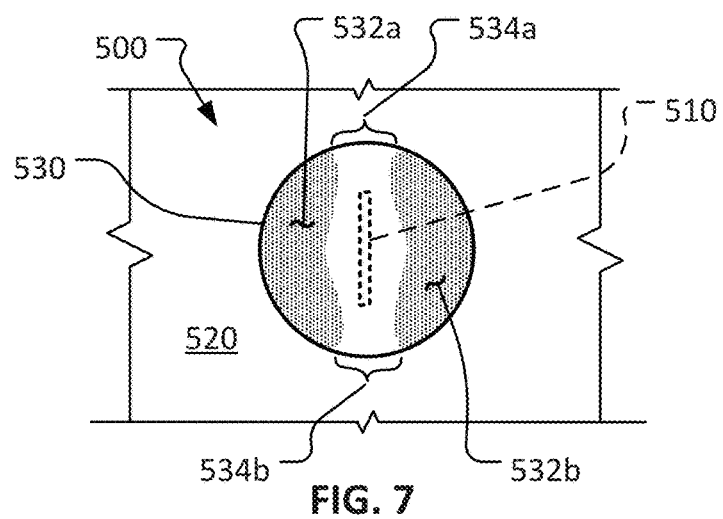
FIG. 7 is a plan view of a portion of another weeping balloon device in accordance with some embodiments.

Referring to FIG. 7, another example weeping balloon 500 can be configured to control the passage of fluid through an opening 510. While a single opening 510 is depicted in this portion of weeping balloon 500, it should be understood that, as described above, any number of such openings 510 can be included in the weeping balloon 500.

In the depicted embodiment, the opening 510 (a slit in this example, but the opening 510 could be a hole of various shapes, etc.) is defined by the balloon wall 520. An overlaid material 530 is attached to the balloon wall 520 such that the overlaid material 530 at least partially covers the opening 510. In the depicted embodiment, the overlaid material 530 fully covers the opening 510.

In some embodiments, the overlaid material 530 is bonded to the balloon wall 520. For example, in the depicted embodiment the overlaid material 530 is bonded to the balloon wall 520 at a first bonded region 532a and a second bonded region 532b. The bonded regions 532a and 532b do not fully surround the opening 510. Instead, at least one open region 534a and/or 534b exists through which fluid can flow. In the depicted embodiment, two open regions 534a and 534b are included. In some embodiments, three, four, or more than four open regions are included. The open regions 534a and 534b allow fluid flowing from opening 510 to flow out onto the balloon wall 520 adjacent to the open regions 534a and 534b. Hence, balloon 500 is a weeping balloon.

The configuration of example weeping balloon 500 can provide a number of functional advantages. First, the overlaid material 530 can stiffen the weeping balloon 500 in the area around the opening 510. Hence, the overlaid material 530 can provide resistance to an enlarging of the opening 510 that may otherwise occur in response to pressurization of the balloon 500. Second, the overlaid material 530 can serve as a one-way valve. That is, while the overlaid material 530 allows fluid flowing from the opening 510 to pass through onto the balloon wall 520 adjacent to the open regions 534a and 534b, the overlaid material 530 will tend to resist fluid flow in the reverse direction. For example, if the pressure exterior to the balloon 500 is greater than the pressure interior to the balloon 500, the overlaid material 530 will be pressed against the balloon wall 520, thereby advantageously sealing the opening 510.

Figure 8:
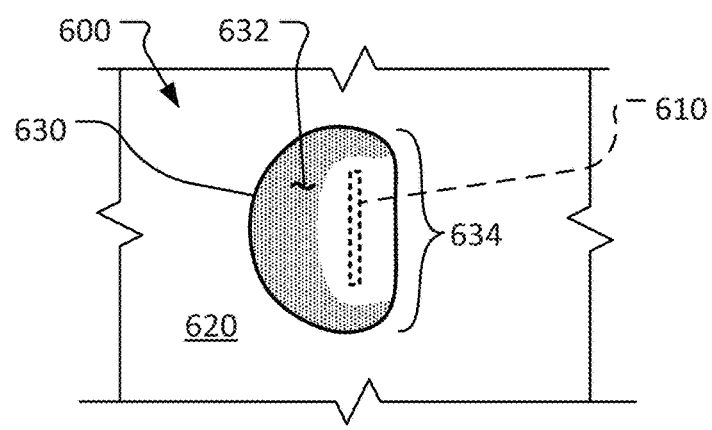
FIG. 8 is a plan view of a portion of another weeping balloon device in accordance with some embodiments.

Referring to FIG. 8, another example weeping balloon 600 can be configured to control the passage of fluid through an opening 610. While a single opening 610 is depicted in this portion of weeping balloon 600, it should be understood that, as described above, any number of such openings 610 can be included in the weeping balloon 600.

In the depicted embodiment, the opening 610 (a slit in this example, but the opening 610 could be a hole of various shapes, etc.) is defined by the balloon wall 620. An overlaid material 630 is attached to the balloon wall 620 such that the overlaid material 630 at least partially covers the opening 610. In the depicted embodiment, the overlaid material 630 fully covers the opening 610.

In some embodiments, the overlaid material 630 is bonded to the balloon wall 620. For example, in the depicted embodiment the overlaid material 630 is bonded to the balloon wall 620 at a bonded region 632. The bonded region 632 does not fully surround the opening 610. Instead, at least one open region 634 (at a free end of the overlaid material 630) exists through which fluid can flow. In some embodiments, two, three, four, or more than four open regions are included. The open region 634 allows fluid flowing from opening 610 to flow out onto the balloon wall 620 adjacent to the open region 634. Hence, balloon 600 is a weeping balloon.

The overlaid material 630 can serve as a one-way valve. That is, while the overlaid material 630 allows fluid flowing from the opening 610 to pass through onto the balloon wall 620 adjacent to the open region 634, the overlaid material 630 will tend to resist fluid flow in the reverse direction. For example, if the pressure exterior to the balloon 600 is greater than the pressure interior to the balloon 600, the overlaid material 630 will be pressed against the balloon wall 620, thereby advantageously sealing the opening 610.

Figure 9:
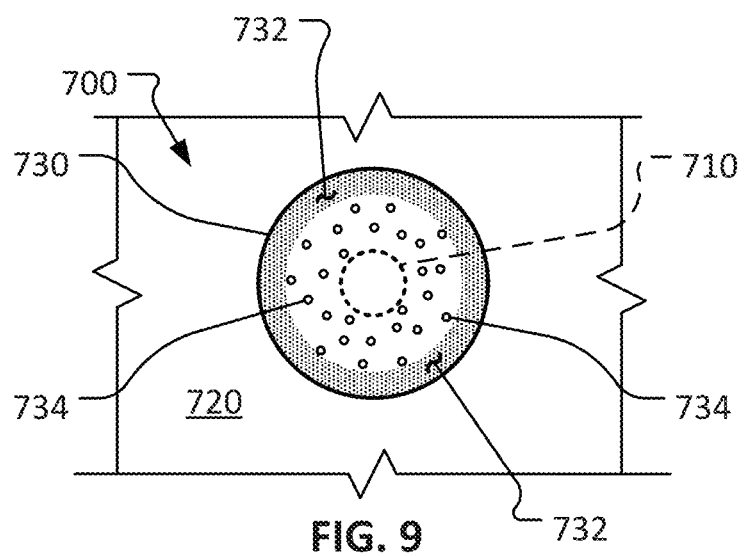
FIG. 9 is a plan view of a portion of another weeping balloon device in accordance with some embodiments.

Referring to FIG. 9, another example weeping balloon 700 can be configured to control the passage of fluid through an opening 710. While a single opening 710 is depicted in this portion of weeping balloon 700, it should be understood that, as described above, any number of such openings 710 can be included in the weeping balloon 700.

In the depicted embodiment, the opening 710 (a circular hole in this example, but the opening 710 could be a slit or a hole of various shapes, etc.) is defined by the balloon wall 720. An overlaid material 730 is attached to the balloon wall 720 such that the overlaid material 730 covers the opening 710.

In some embodiments, the overlaid material 730 is bonded to the balloon wall 720. For example, in the depicted embodiment the overlaid material 730 is bonded to the balloon wall 720 at a bonded region 732. The bonded region 732 fully surrounds the opening 710.

The overlaid material 730 defines a plurality of openings 734. The openings 734 allow fluid flowing from opening 710 to flow out onto the exterior surface of the overlaid material 730. Hence, balloon 700 is a weeping balloon.

The configuration of example weeping balloon 700 can provide a number of functional advantages. First, the overlaid material 730 can stiffen the weeping balloon 700 in the area around the opening 710. Hence, the overlaid material 730 can provide resistance to an enlarging of the opening 710 that may otherwise occur in response to pressurization of the balloon 700. Second, the overlaid material 730 can serve as a one-way valve. That is, while the overlaid material 730 allows fluid flowing from the opening 710 to pass through onto the exterior surface of the overlaid material 730, the overlaid material 730 will tend to resist fluid flow in the reverse direction. That is the case because, in the depicted embodiment, there are no openings 734 that overlapping or that are coincident with the opening 710. Therefore, if the pressure exterior to the balloon 700 is greater than the pressure interior to the balloon 700, the overlaid material 730 will be pressed against the balloon wall 720, thereby advantageously sealing the opening 710.

Figures 10, 11:
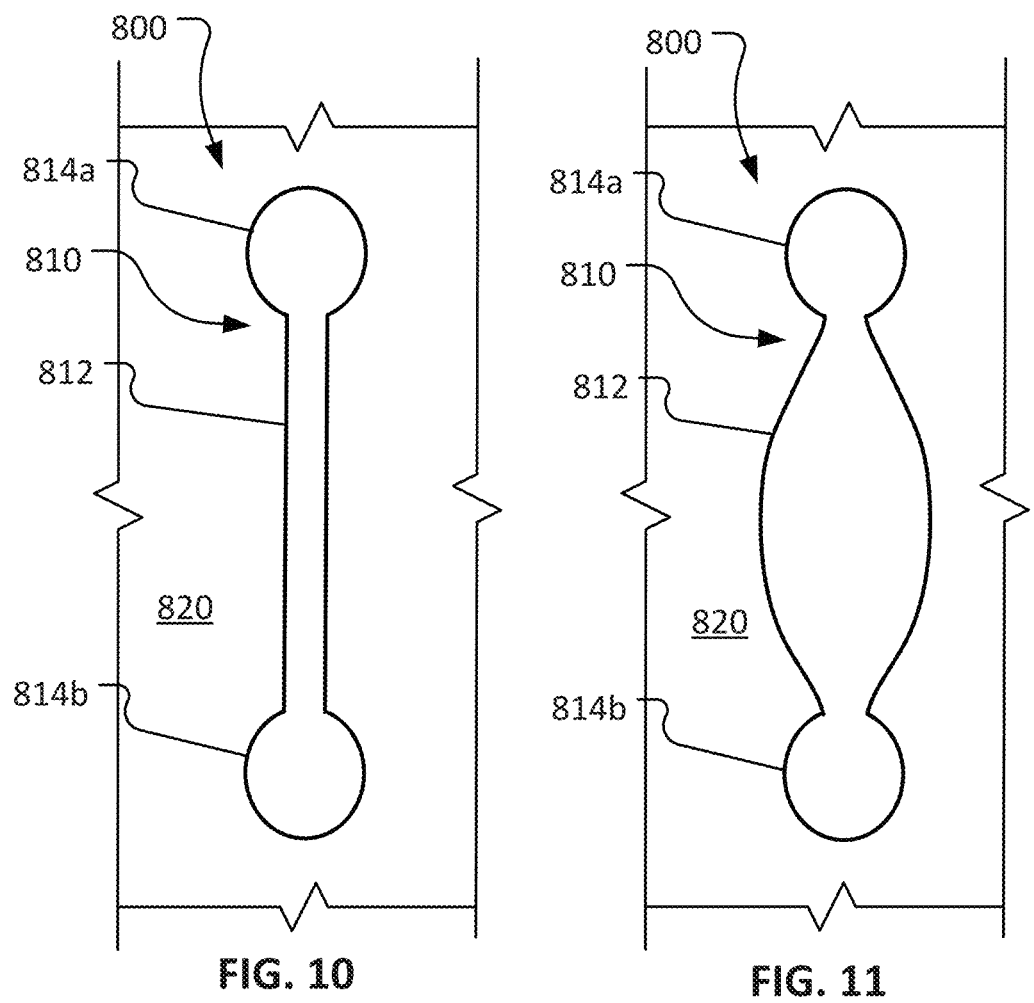
FIG. 10 is a plan view of a portion of another weeping balloon device in accordance with some embodiments.
FIG. 11 is a plan view of the portion of the weeping balloon device of FIG. 10 with the opening in an expanded configuration.

Referring to FIGS. 10 and 11, another example weeping balloon 800 can be configured to control the passage of fluid through an opening 810. While a single opening 810 is depicted in this portion of weeping balloon 800, it should be understood that, as described above, any number of such openings 810 can be included in the weeping balloon 800. In the depicted embodiment, the opening 810 is defined by the balloon wall 820. In FIG. 10, the opening 810 is depicted in an unstressed state. In FIG. 11, the opening 810 is depicted in a stressed state such as would result from fluid flowing outward from the interior of the balloon 800 through the opening 810.

In the depicted embodiment, the opening 810 is a slit that is configured to resist tearing. Opening 810 includes a middle portion 812, a first end 814a, and a second end 814b. The ends 814a and 814b are shaped (i.e., radiused) to advantageously mitigate stress concentrations in the balloon wall 820. Opening 810 may be included in any of the weeping balloon embodiments described herein.

Referring to FIGS. 12 and 13, a weeping balloon 900 can define one or more openings 910 through which fluid can pass. While four openings 910 are depicted on this distal face of weeping balloon 900, it should be understood that, as described above, any number of such openings 910 can be included in the weeping balloon 900. FIG. 12 shows a distal end view of the weeping balloon 900. FIG. 13 shows a cross-sectional view along section line A-A.

Weeping balloon 900 is designed with features that are directed to keeping the size of openings 910 substantially consistent even with fluctuations in the fluid pressure internal to the balloon 900. In particular, weeping balloon 900 includes ribs 930 on the balloon wall 920 in the areas of the openings 910. Both the balloon wall 920 and the ribs 930 define the opening 910.

The ribs 930 supplement the stiffness of balloon wall 920 around openings 910 to provide greater resistance to the deformation of openings 910 that might otherwise occur without the presence of the ribs 930. For example, as the fluid pressure within the internal space defined by the weeping balloon 900 increases, the balloon wall 920 will tend to stretch. The stretching of the balloon wall 920 will tend to enlarge the openings 910. Such enlarging of the openings 910 may be undesirable in some cases. For example, as the openings 910 enlarges, the openings 910 may become too large and, in result, more fluid than desired may be transmitted through openings 910.

To resist the enlarging of openings 910, the material stiffness around openings 910 can be increased by adding the ribs 930. At other areas of the balloon 900, the single layer balloon wall 920 (without the ribs 930) can provide a higher compliance to allow for a desired low-profile collapsibility of balloon 900, for example. In fact, the ribs 930 provide longitudinal structure for the balloon 900. Therefore, by virtue of the ribs 930, the balloon 900 will advantageously tend to collapse into a low-profile cross shape (rather than randomly).

In some embodiments, the ribs 930 are made of the same material as the balloon wall 920. For example, in some embodiments both the balloon wall 920 and the ribs 930 are made of silicone with about a 30 A durometer. In some embodiments, the ribs 930 are made of a different material than the balloon wall 920. For example, in some embodiments the ribs 930 are made of PEBAX® while the balloon wall 920 is made of silicone (e.g., about 30 A durometer). It should be understood that other combinations of materials are also envisioned. In another non-limiting example, the balloon wall 920 is made of silicone at a first durometer (e.g., about 30 A durometer) and the ribs 930 are made of silicone at a second durometer (e.g., about 50 A durometer). Further, in some embodiments the ribs 930 are made of a hydrophilic PEBAX® such as MV1074 SA01 MED (Hydrophilic grade). In some cases, the construction of the ribs 930 can include one or more fibers that provide mechanical reinforcement against deformation of the ribs 930. All foregoing materials and constructions may be used in any of the other embodiments provided herein.

The ribs 930 are attached to the balloon wall 920. In some cases, the ribs 930 and balloon wall 920 are made of a single unitary construct. In some cases, the ribs 930 are molded onto the balloon wall 920 using a two-step molding process. In some cases, an adhesive is used to bond the ribs 930 to the balloon wall 920. For example, in some cases a UV curable silicone adhesive is used to bond the ribs 930 to the balloon wall 920. Other types of adhesives can also be used.

As described above, both the ribs 930 and the balloon wall 920 define the openings 910. In the depicted embodiment, the openings 910 are the same size in each of the ribs 930 and the balloon wall 920. In some embodiments, the opening defined by the ribs 930 is larger than the opening defined by the balloon wall 920. In some embodiments, the opening defined by the ribs 930 is smaller than the opening defined by the balloon wall 920. For example, in some embodiments the diameters of the openings defined by the ribs 930 and the balloon wall 920 differ by about 5% to about 15%, or about 10% to about 20%, or about 15% to about 25%, or about 20% to about 30%, or about 25% to about 35%, or about 30% to about 40%, or more than about 40%.

The openings 910 can be created by various techniques including, but not limited to, cut using a scalpel, die cut, laser cut, or molded in. In some embodiments, the openings 910 do not extend radially from a center of the balloon 900.

While in the depicted embodiment the opening 910 is a slit, in some embodiments the opening 910 has a different shape. For example, in some embodiments the opening 910 is a slot, a circular opening, ovular opening, elliptical opening, rectangular opening, triangular opening, and the like. In some embodiments, different shapes may be used for the openings 910 at different locations on the weeping balloon 900.

Second, the ribs 930 can help the openings 910 to function as one-way valves. That is, while the ribs 930 allow fluid flowing from the opening 910 to pass through onto the exterior surface of the balloon wall 920 and/or the ribs 930, the ribs 930 will tend to resist fluid flow in the reverse direction. For example, if the pressure exterior to the balloon 900 is greater than the pressure interior to the balloon 900, the ribs 930 will be pressed against the balloon wall 920 and/or ribs 930, thereby advantageously sealing the openings 910.

Referring to FIGS. 14 and 15, an example weeping balloon 1000 is depicted in a collapsed low-profile configuration. Weeping balloon 1000 is molded in the shape as depicted. That is, the weeping balloon 1000 is molded to include a plurality of folds defined by the balloon wall 1020. The folds extend radially along generally linear paths.

Referring also to FIGS. 16 and 17, another example weeping balloon 1100 is depicted in a collapsed low-profile configuration. Weeping balloon 1100 is molded in the shape as depicted. That is, the weeping balloon 1100 is molded to include a plurality of folds defined by the balloon wall 1120. The folds extend radially along curved paths.

Referring also to FIGS. 18 and 19, at the crotches 1024 between the folds 1026 of the balloon wall 1020 (using weeping balloon 1000 as a representative example of both weeping balloons 1000 and 1100), one or more openings 1010 can be defined by the balloon wall 1020. FIG. 18 shows a cross-sectional view of a crotch between the folds of the balloon wall 1020 at the location of an opening 1010. FIG. 19 shows the same portion of weeping balloon 1000 when the weeping balloon 1000 is inflated. It should be understood that the openings 1010 can be holes of any shape, or slits, and any other configuration as described herein.

In the deflated configuration of FIG. 18, the opening 1010 is advantageously sealed closed. However, in the inflated configuration of FIG. 19, the opening 1010 is advantageously opened to a controlled extent to allow balloon 1000 to be a weeping balloon.

The thickness of the balloon wall 1020 can be increased (e.g., as shown) around the openings 1010 in some embodiments. In result, the balloon wall 1020 will be stiffer around the openings 1010 to resist enlargement of the openings 1010 while balloon 1000 is inflated.

Figure 22:
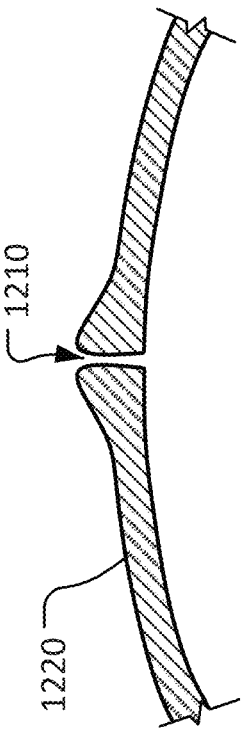
FIG. 22 is a cross-sectional view of a portion of the weeping balloon devices of FIG. 20. The cross-sectional view is shown with the balloon in an inflated configuration.
Figure 21:
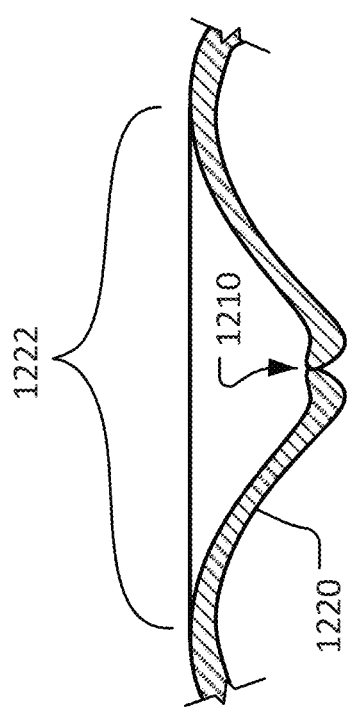
FIG. 21 is a cross-sectional view of a portion of the weeping balloon device of FIG. 20. The cross-sectional view is shown with the balloon in an uninflated configuration.
Figure 20:
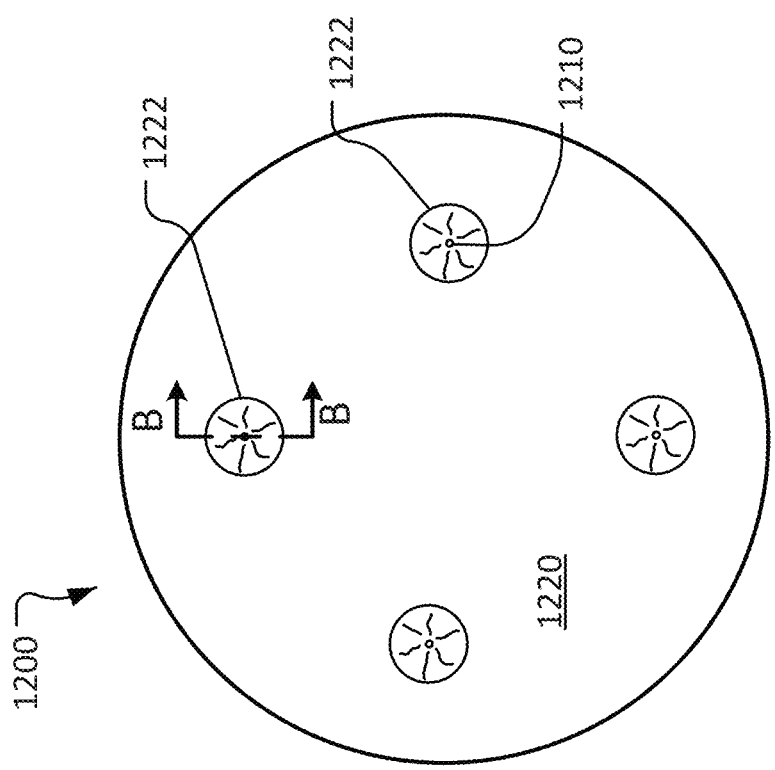
FIG. 20 is a distal end view of another weeping balloon device in accordance with some embodiments.

Referring to FIGS. 20-22, a weeping balloon 1200 can define one or more openings 1210 through which fluid can pass. While four openings 1210 are depicted on this distal face of weeping balloon 1200, it should be understood that, as described above, any number of such openings 1210 can be included in the weeping balloon 1200. FIG. 20 shows a distal end view of the weeping balloon 1200. FIG. 21 shows a cross-sectional view of a first configuration (partially inflated) along section line B-B. FIG. 22 shows a cross-sectional view of a second configuration (fully inflated) along section line B-B.

In some embodiments, the balloon wall 1220 is molded to include one or more localized depressions 1222 in the distal face of the weeping balloon 1200. An opening 1210 can be defined near the center, bottom region of each depression 1222. While the weeping balloon 1200 is partially inflated (as depicted by FIGS. 20 and 21), the openings 1210 are advantageously sealed closed. However, in the fully inflated configuration as shown in FIG. 22, the depressions 1222 expand outward (thereby effectively eliminating the depressions 1222) and the openings 1210 are advantageously opened to a controlled extent to allow balloon 1200 to be a weeping balloon.

The thickness of the balloon wall 1220 can be increased (e.g., as shown) around the openings 1210 in some embodiments. In result, the balloon wall 1220 will be stiffer around the openings 1210 to resist enlargement of the openings 1210 while balloon 1200 is fully inflated.

A number of embodiments of the weeping balloon devices for use with balloon catheter visualization devices and other medical devices, systems, and methods have been described. Nevertheless, it will be understood that various modifications may be made without departing from the spirit and scope of the subject matter described herein. Moreover, it should be understood that the features of one or more of the weeping balloon devices described herein can be combined with features from one or more other weeping balloon devices provided herein. That is, hybrid designs can be created by combining various features and such hybrid designs are fully within the scope of this disclosure. Accordingly, other embodiments are within the scope of the disclosure and the following claims.

What is claimed is:

1. A weeping balloon device comprising:
  a catheter shaft defining a lumen;
  an inflatable balloon attached to the catheter shaft, the inflatable balloon comprising a balloon wall defining an interior space in fluid communication with the lumen, the balloon wall defining a plurality of openings in fluid communication with the interior space, the balloon wall having an increased thickness surrounding each of the plurality of openings that resists inflow of fluid into the interior space, wherein the plurality of openings surrounded by the increased thickness of the balloon wall are conical with a smaller diameter facing the interior space of the inflatable balloon; and
  at each opening of the plurality of openings, an additional layer of material attached to the balloon wall.

2. The device of claim 1, wherein each additional layer of material defines an additional opening that is concentric with a corresponding opening of the plurality of openings defined by the balloon wall.

3. The device of claim 1, wherein at least one of the additional layers of material does not define any openings.

4. The device of claim 3, wherein an open region between the at least one additional layer of material and the balloon wall provides a passageway in fluid communication with the opening through the balloon wall that is at the at least one additional layer of material.

5. The device of claim 1, wherein at least one of the additional layers of material defines a plurality of additional openings that are in fluid communication with the opening through the balloon wall that is at the at least one additional layer of material.

6. The device of claim 5, wherein the plurality of additional openings are smaller than the opening through the balloon wall that is at the at least one additional layer of material.

7. The device of claim 1, wherein at least one opening of the plurality of openings is a slit.

8. The device of claim 1, wherein the additional layer of material is laminated on the balloon wall around each opening.

9. The device of claim 1, wherein the balloon wall is made of a first material and the additional layer of material is made of a second material, wherein the second material has a higher durometer than the first material.

10. A weeping balloon device comprising:
a catheter shaft defining a lumen;
an inflatable balloon attached to the catheter shaft, the inflatable balloon comprising an inner balloon wall defining an interior space in fluid communication with the lumen and an outer balloon wall defining an exterior surface of the balloon, the inner and outer balloon walls defining a plurality of openings in fluid communication with the interior space, wherein one of the inner and outer balloon walls has an increased thickness surrounding each of the plurality of openings that resists inflow of fluid into the interior space; and
an additional layer of material disposed between the inner and outer balloon walls at each opening of the plurality of openings.

11. The device of claim 10, wherein the outer balloon wall has the increased thickness surrounding the plurality of openings.

12. The device of claim 11, wherein the plurality of openings defined by the outer balloon wall are conical with a larger diameter adjacent the exterior surface.

13. The device of claim 10, wherein the additional layer of material is laminated on the inner balloon wall around each opening.

14. The device of claim 13, wherein the inner and outer balloon walls are made of a first material and the additional layer of material is made of a second material, wherein the second material has a higher durometer than the first material.

* * * * *